(12) United States Patent
Imura

(10) Patent No.: US 7,852,481 B2
(45) Date of Patent: Dec. 14, 2010

(54) APPARATUS AND METHOD FOR MEASURING OPTICAL PROPERTY

(75) Inventor: Kenji Imura, Toyohashi (JP)

(73) Assignee: Konica Minolta Sensing, Inc., Osaka (JP)

( * ) Notice: Subject to any disclaimer, the term of this patent is extended or adjusted under 35 U.S.C. 154(b) by 75 days.

(21) Appl. No.: 12/080,061

(22) Filed: Mar. 31, 2008

(65) Prior Publication Data
US 2008/0246969 A1    Oct. 9, 2008

(30) Foreign Application Priority Data
Apr. 3, 2007   (JP) ............................. 2007-097554

(51) Int. Cl.
*G01N 21/55* (2006.01)
(52) U.S. Cl. ................. 356/445; 356/433; 356/256; 356/237.1; 356/237.5; 250/548
(58) Field of Classification Search ................. 356/445, 356/446, 433, 256, 237.1–237.5; 250/548
See application file for complete search history.

(56) References Cited

U.S. PATENT DOCUMENTS

| | | | | |
|---|---|---|---|---|
| 3,804,521 A | * | 4/1974 | Sprague | 356/512 |
| 5,155,558 A | * | 10/1992 | Tannenbaum et al. | 356/446 |
| 5,717,485 A | * | 2/1998 | Ito et al. | 356/237.1 |
| 5,923,434 A | * | 7/1999 | Lex | 356/445 |
| 6,542,248 B1 | * | 4/2003 | Schwarz | 356/600 |
| 6,842,250 B2 | * | 1/2005 | Schwarz | 356/445 |
| 7,391,518 B1 | * | 6/2008 | Schwarz et al. | 356/446 |
| 2006/0187453 A1 | | 8/2006 | Sperling et al. | |
| 2006/0256341 A1 | * | 11/2006 | Kuwada | 356/445 |

FOREIGN PATENT DOCUMENTS

JP       2006-208361       8/2006

* cited by examiner

*Primary Examiner*—Tarifur R. Chowdhury
*Assistant Examiner*—Isiaka O Akanbi
(74) *Attorney, Agent, or Firm*—Brinks Hofer Gilson & Lione

(57) ABSTRACT

An optical property measuring apparatus and an optical property measuring method of the invention determine a specified optical property of a sample by using a distribution function indicating a distribution of the amounts of reflected light incident on an optical sensor along a coordinate axis defined on a light-sensing surface of the optical sensor. Therefore, even when the optical sensor is a light-sensing device provided with a relatively small number of photosensitive elements, it is possible to measure the specified optical property regardless of a position error of the sample, if any, and reduce errors in measurement values caused by such a sample position error.

16 Claims, 10 Drawing Sheets

TO A/D CONVERTER 33

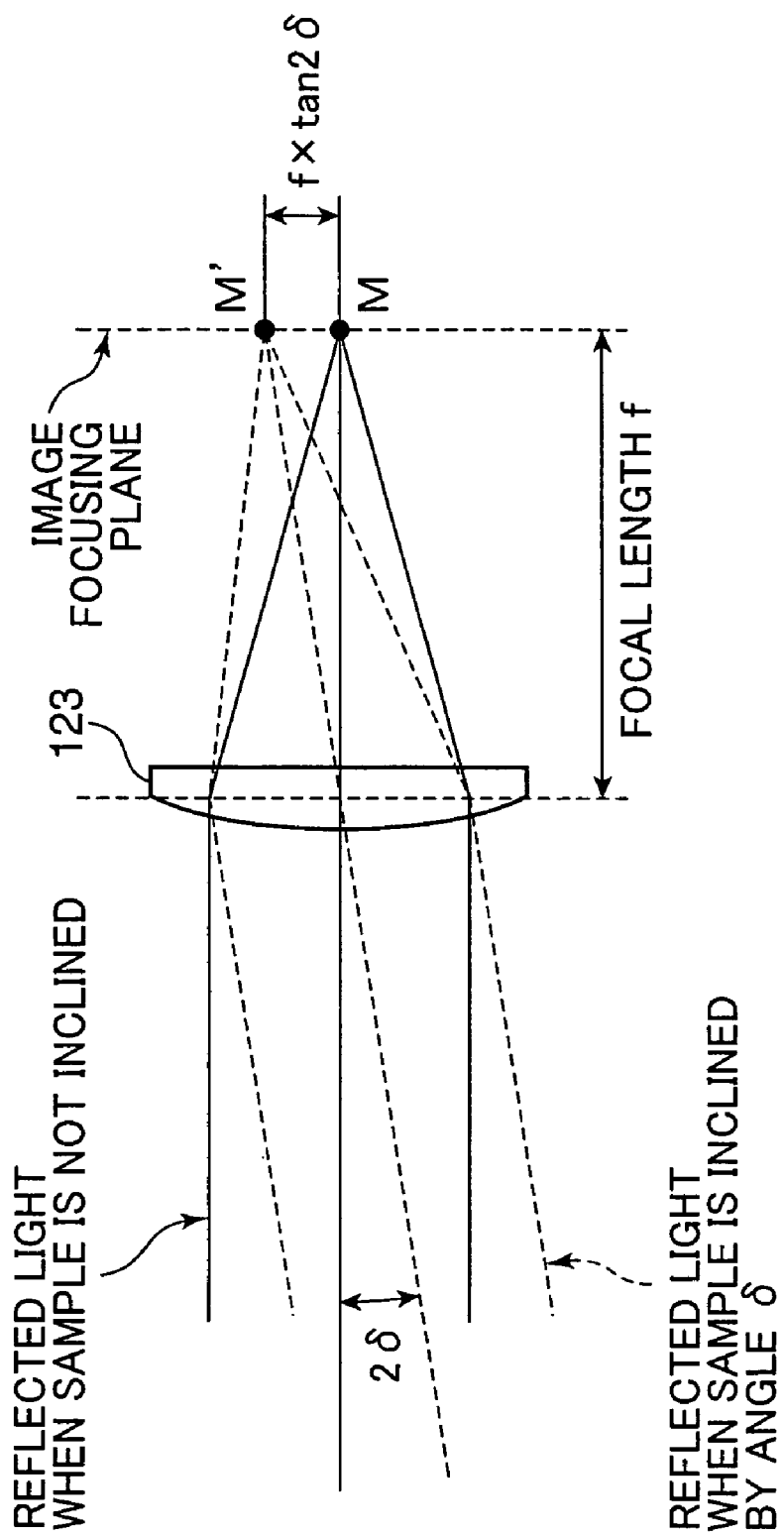

APPARATUS AND METHOD FOR MEASURING OPTICAL PROPERTY

This application is based on Japanese Patent Application No. 2007-97554 filed on Apr. 3, 2007, the contents of which are hereby incorporated by reference.

BACKGROUND OF THE INVENTION

1. Field of the Invention

The present invention relates to an apparatus and a method for measuring optical properties of a sample material, such as an optical surface property, and more particularly glossiness, of the sample material.

2. Description of the Related Art

Optical property measuring apparatuses for measuring optical surface properties of a sample surface, such as glossiness thereof, are conventionally known.

FIG. 9 is a diagram showing the optical configuration of a conventional optical property measuring apparatus, FIG. 10 is a plan view showing the structure of a projection-side aperture plate of the optical property measuring apparatus, FIG. 11 is a plan view showing the structure of a sensing-side aperture plate of the conventional optical property measuring apparatus, and FIG. 12 is a diagram for explaining image focusing positions of a projection-side aperture formed in the projection-side aperture plate.

Referring to FIGS. 9 to 11, the conventional optical property measuring apparatus 100 comprises a projection-side optical system 110 and a sensing-side optical system 120. The projection-side optical system 110 is configured such that an optical axis 113a makes a specific angle θ3 with a normal G to a surface SMa of a sample SM, the normal G passing a particular point on the sample surface SMa, whereas the sensing-side optical system 120 is configured such that an optical axis 123a makes a specific angle θ4 with the normal G.

The projection-side optical system 110 includes a light source 111, the aforementioned projection-side aperture plate 112 and an illumination lens 113. As shown in FIG. 10, the projection-side aperture plate 112 has the aforementioned projection-side aperture 112a formed therethrough. The projection-side aperture 112a has a rectangular shape having a width w of 0.75 degrees (as measured generally in a vertical direction as illustrated in FIG. 9) and a height h of 2.5 degrees (as measured in a direction perpendicular to the plane of paper as illustrated in FIG. 9) in terms of view angle.

On the other hand, the sensing-side optical system 120 includes an optical sensor 121, the aforementioned sensing-side aperture plate 122 and a light-receiving lens 123. As shown in FIG. 11, the sensing-side aperture plate 122 has a sensing-side aperture 122a formed therethrough. The sensing-side aperture 122a has a rectangular shape having a width W of 4.4 degrees (as measured generally in the vertical direction as illustrated in FIG. 9) and a height H of 11.7 degrees (as measured in the direction perpendicular to the plane of paper as illustrated in FIG. 9) in terms of view angle.

A traveling path of light emitted by the light source 111 is confined by the projection-side aperture 112a formed in the projection-side aperture plate 112 to a specific spreading angle and the illumination lens 113 produces a parallel light beam (a beam of parallel light rays) 111a which is generally parallel to the optical axis 113a. The parallel light beam 111a thus produced illuminates the sample surface SMa and incident light is reflected by the sample surface SMa. Part 121a of light reflected generally in a direction of regular reflection is converged by the light-receiving lens 123 and received by the optical sensor 121 after passing through the sensing-side aperture 122a formed in the sensing-side aperture plate 122. Then, the optical property measuring apparatus 100 determines the value of an optical property of the sample surface SMa, such as glossiness thereof, based on an output of the optical sensor 121.

In this optical property measuring apparatus 100, it is required that the sample SM be placed in a "normal" position in order that the sample SM is so disposed relative to the projection-side optical system 110 and the sensing-side optical system 120 as to produce angles of incidence and reflection equal to the aforementioned specific angles θ3 and θ4. However, if the sample SM inclines by angle δ, for example, an image focusing position M' on an image focusing plane is displaced by as much as f·tan 2δ from an image focusing position M obtained when the sample SM is in the normal position, where f is the focal length of the light-receiving lens 123. When the sample SM having a specular surface is in the normal position, an image of the projection-side aperture 112a passes through approximately a central part of the sensing-side aperture 122a as shown by broken lines 112b in FIG. 11 and properly falls upon the optical sensor 121. If the sample SM deviates from the normal position, however, the image of the projection-side aperture 112a will be displaced from the sensing-side aperture 122a and obstructed by the sensing-side aperture plate 122 in part or totally as shown by broken lines 112c in FIG. 11 so that the image will not properly falls upon the optical sensor 121. In this case, the optical sensor 121 can not receive an amount of light that is expected to be obtainable under normal conditions and, as a consequence, values of the measured optical property contain some errors. Also, if the sample SM does not have a specular surface, the reflected light is scattered so that the measured optical property values contain errors in this case as well.

This kind of inconvenience occurs not only when the sample SM inclines from the normal position, causing a position error thereof, but also when the surface SMa of the sample SM is not a flat surface.

Under such circumstances, Japanese Unexamined Patent Publication No. 2006-208361 proposes an arrangement for overcoming the aforementioned problem of the prior art. Specifically, the arrangement of this Publication is to eliminate the aforementioned sensing-side aperture plate 122 and employ instead of the optical sensor 121 an image pickup device having a large light-sensing surface provided with a relatively large number of photosensitive elements (pixels) made of charge-coupled devices (CCDs), for example. In this arrangement, a pixel area corresponding to the aforementioned sensing-side aperture 122a is defined on the light-sensing surface of the image pickup device at a location thereof on which light reflected by a sample is incident in order to solve the problem of the prior art.

For measuring optical properties with high accuracy, however, a charge-transfer image pickup device provided with a relatively large number of photosensitive elements like CCDs does not provide satisfactory basic performance with respect to signal-to-noise ratio (S/N ratio) of an output, linearity and temperature characteristics of the device, for instance.

A photodiode array, on the other hand, has superb basic performance to offer improved measuring accuracy. There are however limitations in circuit configuration and cost-effectiveness of an arrangement employing a photodiode array for directly taking out outputs from individual photosensitive elements (photodiodes). It is therefore impossible to use a photodiode array provided with a relatively large number of photosensitive elements like the CCD-based image pickup device.

SUMMARY OF THE INVENTION

The present invention is intended to overcome the aforementioned problems of the prior art. Accordingly, it is an object of the invention to provide an optical property measuring apparatus and an optical property measuring method which make it possible to reduce errors in measurement values caused by a position error of a sample, if any, by using a light-sensing device provided with a relatively small number of photosensitive elements.

According to an optical property measuring apparatus and an optical property measuring method of the invention, A distribution function is obtained based on an output from an optical sensor for detecting reflected light, a specified optical property of a sample is determined by using the distribution function. The distribution function indicates a distribution of the amounts of the reflected light incident on the optical sensor along a coordinate axis defined on a light-sensing surface of the optical sensor. Therefore, even when the optical sensor is a light-sensing device provided with a relatively small number of photosensitive elements, it is possible to measure the specified optical property regardless of a position error of the sample, if any, and reduce errors in measurement values caused by such a sample position error.

The foregoing and other objects, features, aspects and advantages of the present invention will become more apparent from the following detailed description when read in conjunction with the accompanying drawings.

BRIEF DESCRIPTION OF THE DRAWINGS

FIG. 12 is a diagram for explaining image focusing positions of a projection-side aperture formed in the projection-side aperture plate.

DETAILED DESCRIPTION OF THE PREFERRED EMBODIMENT OF THE INVENTION

A preferred embodiment of the present invention is now described with reference to the accompanying drawings, in which elements designated by the same symbols have the same configuration and explanation thereof may be omitted as appropriate.

Figure 1:
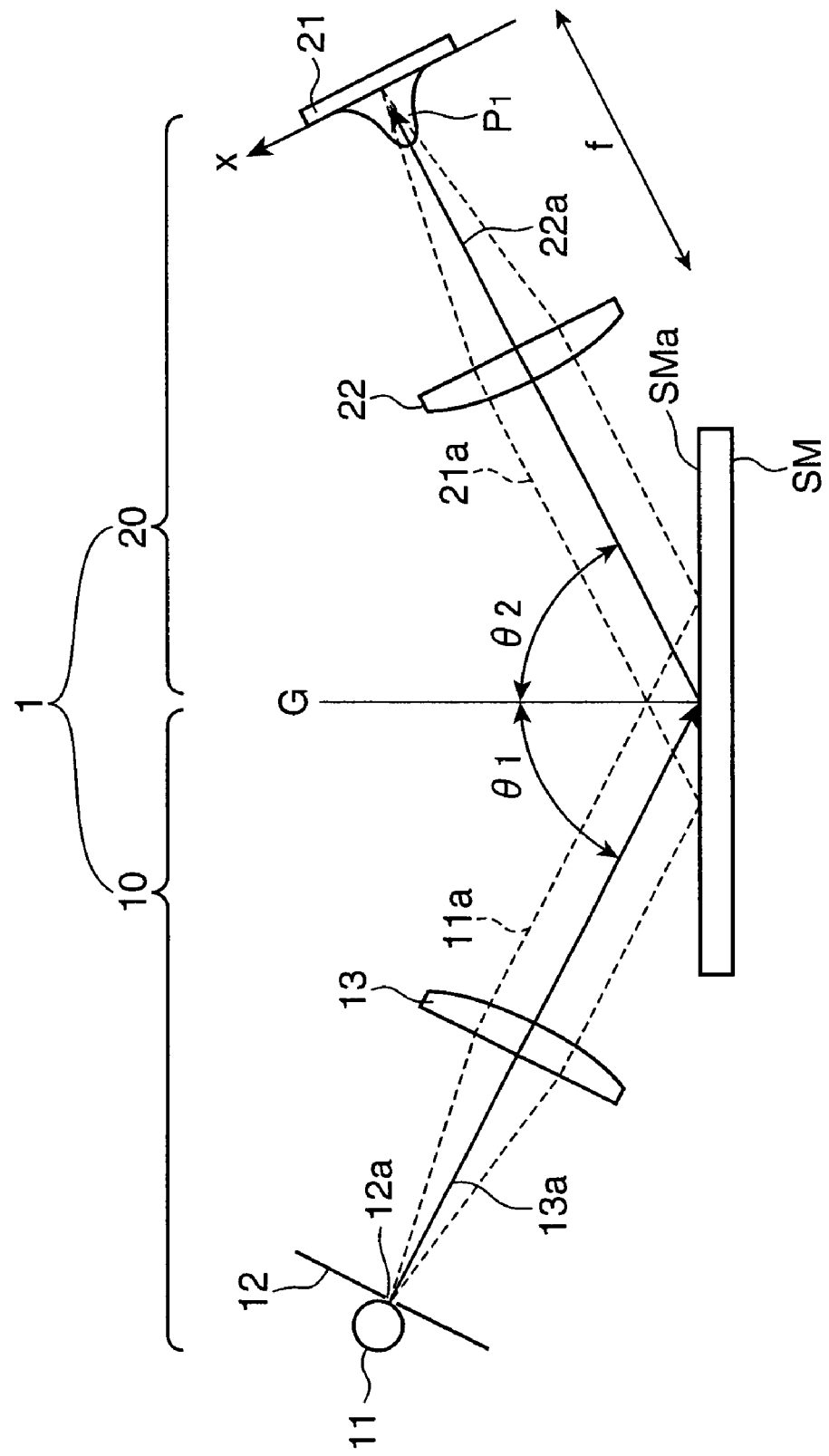
FIG. 1 is a diagram showing the optical configuration of an optical property measuring apparatus according to a preferred embodiment of the invention.
Figure 2:
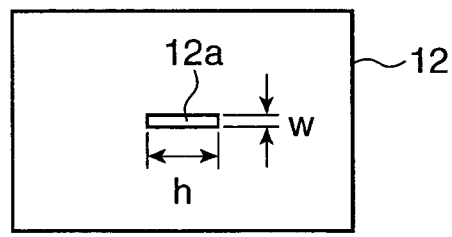
FIG. 2 is a plan view showing the structure of an aperture plate of the optical property measuring apparatus of the embodiment.
Figure 3:
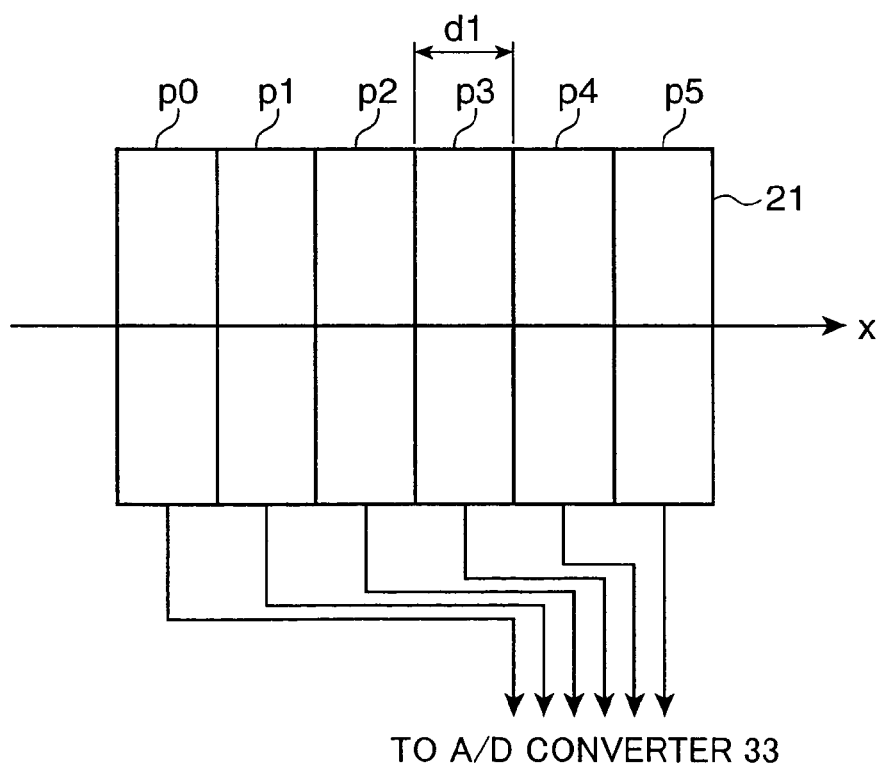
FIG. 3 is a diagram showing the configuration of an optical sensor of the optical property measuring apparatus of the embodiment.
Figure 4:
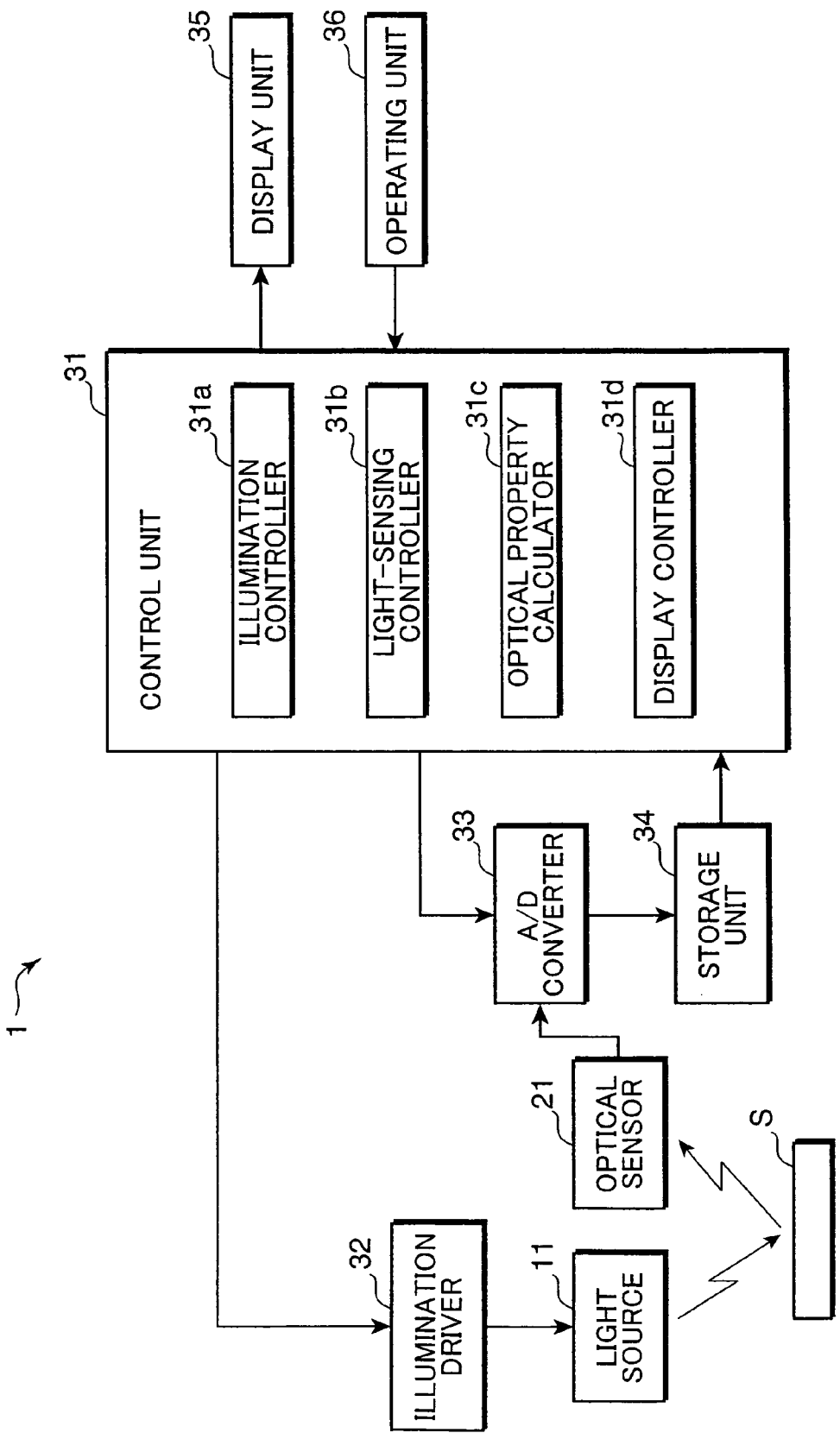
FIG. 4 is a block diagram showing the electrical configuration of the optical property measuring apparatus of the embodiment.

FIG. 1 is a diagram showing the optical configuration of an optical property measuring apparatus according to the preferred embodiment of the invention, FIG. 2 is a plan view showing the structure of an aperture plate of the optical property measuring apparatus of the embodiment, FIG. 3 is a diagram showing the configuration of an optical sensor of the optical property measuring apparatus of the embodiment, and FIG. 4 is a block diagram showing the electrical configuration of the optical property measuring apparatus of the embodiment.

First, the optical configuration of the optical property measuring apparatus 1 of the embodiment is described below. Referring to FIGS. 1 to 3, the optical property measuring apparatus 1 comprises a projection-side optical system 10 for projecting light on a specified area of a surface SMa of a sample SM and a sensing-side optical system 20 for receiving light reflected from the specified area of the sample surface SMa.

The projection-side optical system 10 and the sensing-side optical system 20 are provided on opposite sides of a normal G to the sample surface SMa passing a particular point on the sample surface SMa. When the sample SM is in a normal position, an optical axis 13a of the projection-side optical system 10 makes a specific angle θ1 with the normal G to the sample surface SMa, whereas an optical axis 22a of the sensing-side optical system 20 makes a specific angle θ2 with the normal G to the sample surface SMa. While the angles θ1 and θ2 may be any arbitrary angles, these angles of incidence and reflection are defined to be 20 degrees, 60 degrees or 85 degrees in a technical standard of the International Standardization Organization (ISO) and a Japanese Industrial Standard (JIS) of the Japanese Standards Association. In this embodiment, the angles θ1 and θ2 are set to 60 degrees for measuring 60-degree glossiness according to the Standard Test Method for Specular Gloss ASTM D523 stipulated by the American Society for Testing and Materials (ASTM). Therefore, the projection-side optical system 10 and the sensing-side optical system 20 are arranged such that the optical axis 13a of the projection-side optical system 10 and the optical axis 22a of the sensing-side optical system 20 are in mirror-image symmetry in which the normal G to the sample surface SMa forms an axis of symmetry.

The projection-side optical system 10 includes a light source 11, the aforementioned projection-side aperture plate 12 and an illumination lens 13 which are arranged in this order from a farthest distance toward the sample surface SMa with optical axes of the light source 11, the aperture plate 12 and the illumination lens 13 aligned with the optical axis 13a of the projection-side optical system 10.

The light source 11 is a device configured with such light-emitting elements as light-emitting diodes (LEDs) for projecting light toward the sample surface SMa. The aperture plate 12 is a device for confining the light emitted by the light source 11 toward the sample surface SMa to a specific spreading angle. The aperture plate 12 is, for example, a platelike member made of a material capable of interrupting a wavelength of such a light component contained in the light emitted by the light source 11 that is to be projected on the sample surface SMa, the aperture plate 12 having an aperture 12a formed therethrough as shown in FIG. 2. This aperture 12a has a rectangular shape having a width w of 0.75 degrees (as measured generally in a vertical direction as illustrated in FIG. 1) and a height h of 2.5 degrees (as measured in a direction perpendicular to the plane of paper as illustrated in FIG. 1) in terms of view angle. The illumination lens 13 is an optical device for transforming the light which has passed through the aperture 12a in the aperture plate 12 into a parallel light beam 11a which is generally parallel to the optical axis 13a and for guiding this parallel light beam 11a toward the sample surface SMa.

The sensing-side optical system 20 includes the aforementioned optical sensor 21 and a light-receiving lens 22 which are arranged in this order from a farthest distance toward the sample surface SMa with optical axes of the optical sensor 21 and the light-receiving lens 22 aligned with the optical axis 22a of the sensing-side optical system 20. The light-receiving lens 22 is an optical device for converging reflected light from the surface SMa of the sample SM and guiding the light toward a light-sensing surface of the optical sensor 21.

The optical sensor 21 includes a plurality of photosensitive elements which are photoelectric conversion elements for converting light energy into electrical energy. In this embodiment, the optical sensor 21 is configured such that outputs of the individual photosensitive elements can be directly taken out therefrom. The optical sensor 21 has the light-sensing surface which is larger than an area from which a specified optical property is to be determined, the optical sensor 21 including photosensitive elements from several to the number in the order of ten. As the sample surface SMa illuminated by the projection-side optical system 10 reflects incident light and the optical sensor 21 receives part 21a of light reflected by the sample surface SMa generally in a direction of regular reflection, the individual photosensitive elements of the optical sensor 21 output electric signals corresponding to the amounts of received light.

In the above-described configuration of the optical property measuring apparatus 1 comprising the projection-side optical system 10 and the sensing-side optical system 20, the optical sensor 21 is mounted in such a manner that the aperture 12a in the aperture plate 12 and the light-sensing surface of the optical sensor 21 are positioned at optically conjugate locations. The size of the light-sensing surface of the optical sensor 21 and focal length f of the light-receiving lens 22 are determined such that the light reflected in the direction of regular reflection falls on the light-sensing surface of the optical sensor 21 as long as a change in the position of the sample SM is not larger than a preset angle.

Specifically, the optical sensor 21 of this embodiment is configured with a silicon photodiode array including six photosensitive elements p0-p5 arranged along one direction of which analog outputs can be individually taken out as shown in FIG. 3, for example. The optical sensor 21 is mounted at a location corresponding to the focal length f of the light-receiving lens 22 in such a manner that, when the surface SMa of the sample SM is a specular surface and an image of the aperture 12a in the aperture plate 12 is formed on the light-sensing surface of the optical sensor 21, the direction along which the photosensitive elements p0-p5 are arranged, corresponds to the direction of the width w of the aperture 12a.

Next, the electrical configuration of the optical property measuring apparatus 1 of the embodiment is described. Referring to the block diagram of FIG. 4, the optical property measuring apparatus 1 comprises, in addition to the aforementioned light source 11 and optical sensor 21, a control unit 31, an illumination driver 32, an analog-to-digital (A/D) converter 33, a storage unit 34, a display unit 35 and an operating unit 36.

The light source 11 and the optical sensor 21 correspond to those shown in FIG. 1. The illumination driver 32 is a circuit which causes the light source 11 to project light corresponding to a control command fed from the control unit 31. The A/D converter 33 is a circuit which converts the analog outputs of the individual photosensitive elements of the optical sensor 21 into digital signals made up of multiple bits (e.g., 8 bits or 10 bits). The analog outputs of the individual photosensitive elements of the optical sensor 21 are input into the A/D converter 33 in parallel or serial format. The storage unit 34 is a circuit for temporarily storing the digital signals input from the A/D converter 33. The storage unit 34 is used as a work area in which the control unit 31 performs various processing operations on the digital signals.

The display unit 35 is a circuit for displaying operation results of the operating unit 36 and values of the measured optical property of the sample SM, such as glossiness thereof, obtained by the control unit 31, the display unit 35 including such a display device as a liquid crystal display (LCD) or an organic electroluminescent (EL) display. The operating unit 36 includes a power on/off circuit for turning on and off mains power supply to the optical property measuring apparatus 1 and a switch circuit through which a measurement start command is entered to initiate measurement of a specified optical property.

The control unit 31 is a circuit for controlling various components of the optical property measuring apparatus 1 mentioned above according to functions thereof in order to measure the specified optical property of the sample SM. As an example, the control unit 31 is configured with a microcomputer including a storage device storing a control program, a microprocessor operated according to the control program and a peripheral circuit thereof, for example. The storage device includes a nonvolatile read-only memory (ROM), a volatile electrically erasable programmable ROM (EEPROM) and volatile random access memory (RAM), for example. The control unit 31 incorporates such functional units as an illumination controller 31a, a light-sensing controller 31b, an optical property calculator 31c and a display controller 31d.

The illumination controller 31a controls operation of the illumination driver 32. More specifically, the illumination controller 31a causes the light source 11 to project light for a specified period of time through the illumination driver 32 when a measurement start command is entered to initiate measurement of the optical property of the sample SM is entered from the operating unit 36. The light-sensing controller 31b controls operation of the A/D converter 33. More specifically, the light-sensing controller 31b causes the A/D converter 33 to perform operation for converting the analog outputs of the optical sensor 21 into digital signals in synchronism with illumination timing of the light source 11 when the measurement start command is entered to initiate measurement of the optical property of the sample SM is entered from the operating unit 36. The optical property calculator 31c calculates the optical property of the sample SM based on the digital signals fed from the A/D converter 33. In this embodiment, the optical property calculator 31c produces a distribution function $P(x)$ indicating a distribution of the amounts of the reflected light incident on the optical sensor 21 along a coordinate axis (x-axis) defined on the light-sensing surface of the optical sensor 21 based on the outputs thereof, integrates the distribution function $P(x)$ within a specific range and calculates the specified optical property of the sample SM based on an integral value obtained by integrating the distribution function P(x). The display controller 31d displays an optical property value calculated by the optical property calculator 31c on the display unit 35.

Figure 5:
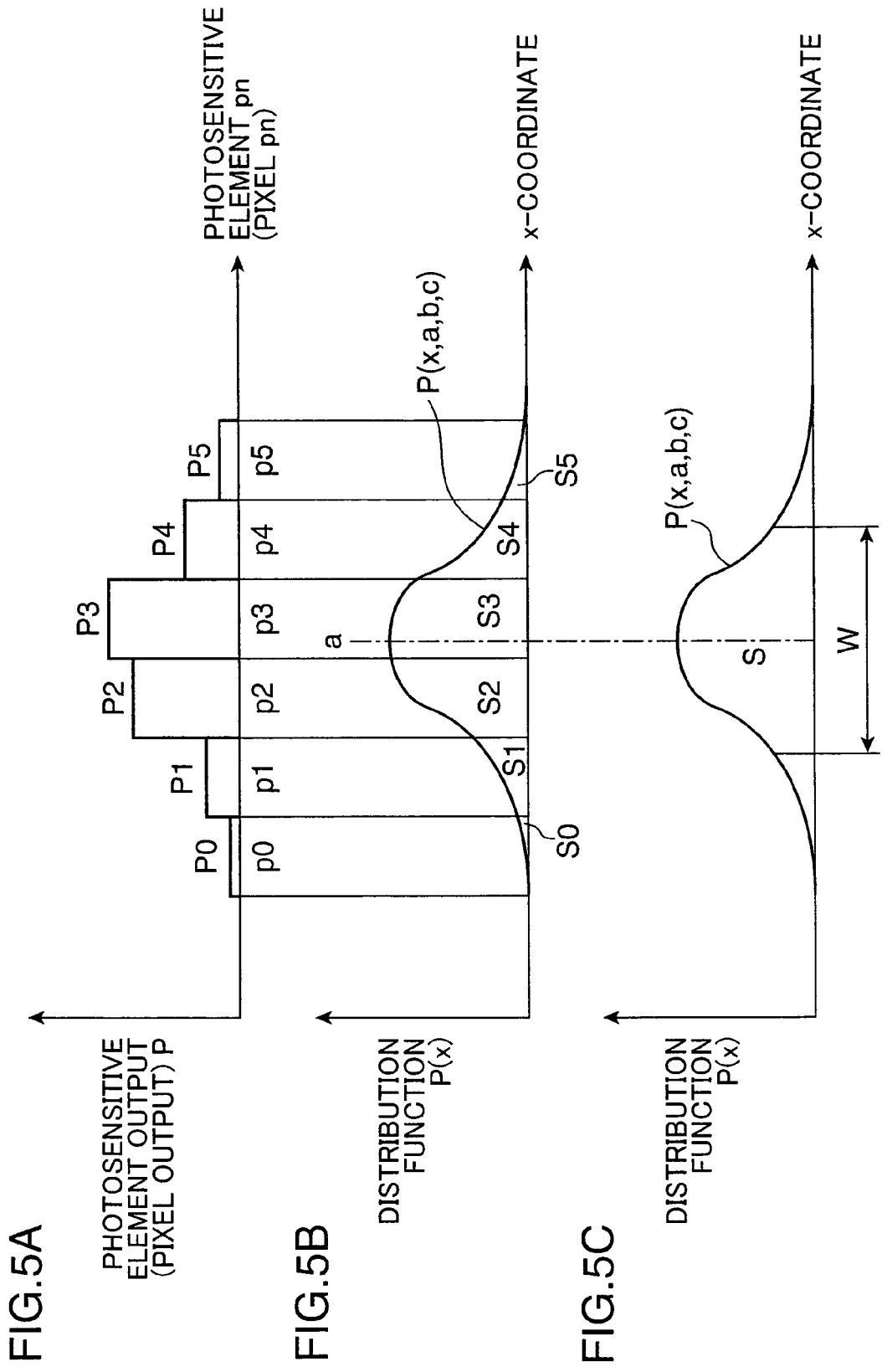
FIGS. 5A-5C are diagrams for explaining a procedure for calculating an optical property according to the embodiment.

Now, the working of the optical property measuring apparatus 1 is described with reference to FIGS. 5A-5C which are diagrams for explaining a procedure for calculating the optical property according to the embodiment. FIG. 5 is diagrams for explaining a procedure for calculating an optical property according to the embodiment. FIG. 5A shows an example of output values of the individual photosensitive elements of the optical sensor 21, a horizontal axis representing the arrangement direction of the photosensitive elements pn (where n=0 to 5) and a vertical axis representing the output values Pn of the individual photosensitive elements pn. FIG. 5B shows the distribution function P(x) which approximates the outputs of the optical sensor 21. FIG. 5C shows a range of integration of the distribution function P(x) for determining the optical property value. Horizontal axes of FIGS. 5B and 5C correspond to the aforementioned x-axis and vertical axes of FIGS. 5B and 5C represent the value of the distribution function P(x). The x-axis is defined to coincide with the arrangement direction of the individual photosensitive elements p0-p5 as shown in FIGS. 1 and 3.

When a user places the sample SM in position in the optical property measuring apparatus 1 and enters a measurement start command to initiate measurement of the optical property through the operating unit 36, the illumination controller 31a of the control unit 31 causes the light source 11 to project light.

The light emitted by the light source 11 is confined to the aforementioned specific spreading angle by the aperture 12a formed in the aperture plate 12 and the illumination lens 13 converts the light into the parallel light beam 11a which is oriented generally parallel to the optical axis 13a to hit the surface SMa of the sample SM. Then, the part 21a of light reflected by the sample surface SMa generally in the direction of regular reflection is converged by the light-receiving lens 22 and received by the optical sensor 21. As is understood from the foregoing discussion, the optical property measuring apparatus 1 of the present embodiment is not provided with a member corresponding to the sensing-side aperture plate 122 mentioned earlier with reference to the prior art. Instead, the light reflected by the surface SMa of the sample SM and passed through the light-receiving lens 22 is detected by the optical sensor 21.

Generally, reflected light contains Lambertian diffuse light oriented about a direction of the normal to a sample surface and scattered light oriented about the direction of regular reflection. The glossier the sample surface (i.e., the more the sample surface approaches a perfect mirror surface), the smaller proportion the Lambertian diffuse light oriented about the normal direction constitutes and the larger proportion the scattered light oriented about the direction of regular reflection constitutes, resulting in a decrease in the magnitude of a distribution of the reflected light. On the contrary, the lower the glossiness of the sample surface, the larger proportion the Lambertian diffuse light constitutes and the smaller proportion the scattered light oriented about the direction of regular reflection constitutes.

The light-sensing controller 31b of the control unit 31 causes the A/D converter 33 to perform the operation for converting the analog outputs of the optical sensor 21 into digital signals in synchronism with the illumination timing of the light source 11. In this embodiment, the optical sensor 21 includes the six photosensitive elements p0-p5 and the analog outputs of the individual photosensitive elements p0-p5 are converted into digital signals by the A/D converter 33 as mentioned earlier. For example, the photosensitive element p0 outputs a photosensitivity detected output value P0 as shown in FIG. 5A. Similarly, the photosensitive element p1 outputs a photosensitivity detected output value P1, the photosensitive element p2 outputs a photosensitivity detected output value P2, the photosensitive element p3 outputs a photosensitivity detected output value P3, the photosensitive element p4 outputs a photosensitivity detected output value P4, and the photosensitive element p5 outputs a photosensitivity detected output value P5. In the example shown in FIG. 5A, the photosensitivity detected output value P3 of the photosensitive element p3 is the largest so that the image of the aperture 12a in the aperture plate 12 is formed centering on the photosensitive element p3.

The optical property calculator 31c of the control unit 31 produces the distribution function P(x) indicating the distribution of the amounts of the reflected light incident on the optical sensor 21 along a straight line extending in one direction defined on the light-sensing surface of the optical sensor 21, e.g., along the x-axis shown in FIGS. 1 and 3, based on the outputs of the optical sensor 21. To be more specific, the optical property calculator 31c of the control unit 31 approximates the outputs of the optical sensor 21 by the one-dimensional distribution function P(x).

Due to optical properties of the surface SMa of the sample SM, such as glossiness thereof, the reflected light from the sample surface SMa contains Lambertian diffuse light oriented about the direction of the normal G to the sample surface SMa and scattered light oriented about the direction of regular reflection. The distribution of the amounts of the reflected light incident on the optical sensor 21 can be approximated by equation (1) below (refer to "LightTools Core Module User's Guide Version 5.1," pp. 121-125, "Optical Research Associates," for example):

$$P(x) = \int_{x0-1/2}^{x0+1/2} F(x, a) da \quad (1)$$

WHERE $F(x, a) = L \cdot \cos(\theta) + S \cdot \cos^N(\alpha - \alpha 0)$ $\alpha = \operatorname{atan}(x/f)$ $\alpha 0 = \operatorname{atan}(a/f)$ $\theta = 60° - \alpha + \operatorname{atan}(x0/f)/2$ In equation (1) above, f designates the focal length of the light-receiving lens 22, x0 designates a center coordinate of the distribution of the amounts of the reflected light incident on the optical sensor 21, N designates a numeral value which depends on the degree of glossiness of the sample surface SMa, L designates central intensity of the Lambertian diffuse light oriented about the direction of the normal G to the sample surface SMa, S designates central intensity of the scattered light oriented about the direction of regular reflection, designates the width of the image formed on the optical sensor 21 when the sample surface SMa is a specular surface, and θ designates an angle that a ray of light incident at a coordinate x forms with the normal G to the sample surface SMa. It is understood from above that when the focal length f of the light-receiving lens 22 is known, the distribution function P(x) can be obtained by substituting the center coordinate x0 of the distribution of the amounts of the reflected light incident on the optical sensor 21, the numeral value N which depends on the degree of glossiness of the sample surface SMa, the central intensity L of the Lambertian diffuse light, the central intensity S of the scattered light oriented about the direction of regular reflection and the image width l in equation (1).

Accordingly, the optical property calculator 31c determines the center coordinate x0 of the distribution of the amounts of the reflected light incident on the optical sensor 21, the numeral value N which depends on the degree of glossiness of the sample surface SMa, the central intensity L of the Lambertian diffuse light, the central intensity S of the scattered light oriented about the direction of regular reflection and the image width l of equation (1) by using the photosensitivity detected output values P0-P5 of the individual photosensitive elements p0-p5 of the optical sensor 21 and, then, obtains the distribution function P(x) to thereby approximate the outputs of the optical sensor 21. More specifically, the optical property calculator 31c produces the distribution function P(x) in such a manner that individual integral values S0-S5 obtained by integrating the distribution function P(x) of equation (1) within the specific range corresponding to light-sensitive areas of the individual photosensitive elements p0-p5 will coincide most closely with the photosensitivity detected output values P0-P5 of the individual photosensitive elements p0-p5 as shown in FIGS. 5A and 5B and thereby approximates the outputs of the optical sensor 21. Still more specifically, the optical property calculator 31c determines the values of constants x0, N, L, S and l and produces the distribution function P(x) in such a manner that an error sum of squares D expressed by equation (2) below is minimized, and thereby approximates the outputs of the optical sensor 21. The error sum of squares D given by equation (2) is the sum of squares of errors between the output values P0-P5 of the photosensitive elements p0-p5 and the integral values S0-S5 obtained by integrating the distribution function P(x) of equation (1) within the range corresponding to the light-sensitive areas of the respective photosensitive elements p0-p5.

$$D = \sum_{n=0}^{n=5} (Sn - Pn)^2 \quad (2)$$

Subsequently, the optical property calculator 31c integrates the distribution function P(x) thus obtained within the aforementioned specific range (integration range: x0−W/2 to x0+W/2) corresponding to the width W (=4.4 degrees) of the sensing-side aperture 122a formed in the sensing-side aperture plate 122 of the earlier-described prior art to obtain an integral value S as shown in FIG. 5C, wherein the integration range (x0−W/2 to x0+W/2) is centered on the center coordinate x0 of the distribution function P(x). Specifically, the optical property calculator 31c calculates an integral value S of the distribution function P(x) by equation (3) below:

$$S = \int_{x0-W/2}^{x0+W/2} P(x)dx \quad (3)$$

As the distribution function P(x) is produced in the aforementioned fashion, even when the image of the aperture 12a in the aperture plate 12 is formed at a position on the light-sensing surface of the optical sensor 21 displaced from an ordinary image focusing position obtained when the sample SM is in the normal position, the integral value S calculated as described above remains approximately the same as obtained when the sample SM is in the normal position.

Figure 11:
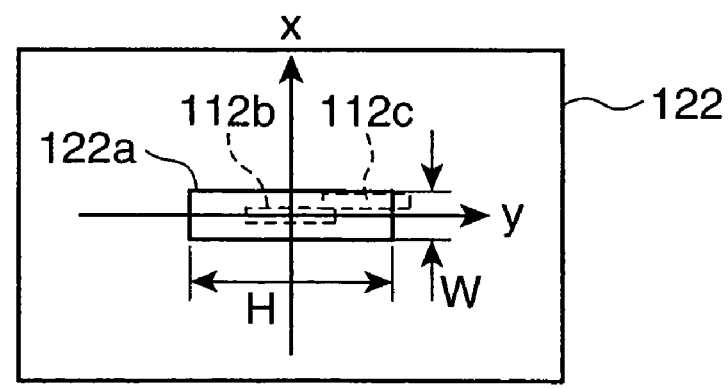
FIG. 11 is a plan view showing the structure of a sensing-side aperture plate of the conventional optical property measuring apparatus.

In the earlier-described optical property measuring apparatus 100 of the prior art, an area from which the optical property is to be determined, such as a light-sensitive area of the aperture plate 121 corresponding to the sensing-side aperture 122a shown in FIG. 11 from which the aperture plate 121 outputs information on the amounts of received light used for calculation of the optical property, is mechanically restricted. This is because the light guided to the light-sensing surface of the aperture plate 121 could be obstructed by the sensing-side aperture plate 122 having the sensing-side aperture 122a that is placed in a light path between the light-receiving lens 123 and the optical sensor 121. In contrast, the optical property measuring apparatus 1 of the present embodiment is configured in such a fashion that no member corresponding to the sensing-side aperture plate 122 of the prior art is placed in a light path between the light-receiving lens 22 and the optical sensor 21 but the optical property calculator 31c integrates the distribution function P(x) within the integration range W corresponding to the width W of the sensing-side aperture 122a, so that the area from which the optical property is to be determined is numerically (mathematically) restricted.

For high-accuracy determination of the intended optical property, it is preferable that a plurality of photosensitive elements be contained in the area of the optical sensor 21 corresponding to the integration range W. Therefore, in a more specific sense, it is preferable that width d1 of each of the photosensitive elements p0-p5 of the optical sensor 21 along the photosensitive element arrangement direction be equal to or less than one-half of the width W of the sensing-side aperture 122a formed in the sensing-side aperture plate 122 (d1≦W/2).

Subsequently, the optical property calculator 31c converts the integral value S calculated as described above into a value of the optical property, such as glossiness, by using a predefined conversion table or a conversion formula. The display controller 31d of the control unit 31 then presents the optical property value thus obtained on the display unit 35.

Configured to operate in the above-described manner, the optical property measuring apparatus 1 can measure the specified optical property of the sample SM even when the optical sensor 21 is a light-sensing device like a photodiode array provided with a relatively small number of photosensitive elements regardless of a position error of the sample SM, if any, making it possible to reduce errors in measurement values caused by such a sample position error. Since the optical sensor 21 is configured with the photodiode array having superb basic performance with respect to S/N ratio of an output, linearity and temperature characteristics, the optical property measuring apparatus 1 can measure the specified optical property with higher accuracy as compared to a case where the optical sensor 21 employs a charge-transfer image pickup device.

While equation (1) used for approximating the outputs of the optical sensor 21 in the above-described embodiment is a function which formulates a distribution of intensities of the scattered light oriented about the direction of regular reflection using $\cos^N$ as basic form, the embodiment may be so modified as to formulate the distribution of the intensities of the scattered light oriented about the direction of regular reflection by equation (4) below using a Gaussian function as basic form:

$$P(x) = \int_{x_0-1/2}^{x_0+1/2} F(x, a) da \quad (4)$$

WHERE $F(x, a) = L \cdot \cos(\theta) + S \cdot \exp((-1/2) \cdot (\alpha - \alpha 0)^2 / d^2)$ $\alpha = \operatorname{atan}(x/f)$ $\alpha 0 = \operatorname{atan}(a/f)$ $\theta = 60° - \alpha + \operatorname{atan}(x0/f)/2$ and d is the magnitude of the distribution that is dependent on the degree of glossiness.

Also, the optical property measuring apparatus 1 of the above-described embodiment may be so modified as to correct the integral value S based on the outputs of the optical sensor 21. By correcting the integral value S in this way, it becomes possible to measure the optical property with yet higher accuracy.

In this case, the optical property calculator 31c of the control unit 31 is so modified as to correct the integral value S calculated by equation (3) based on the photosensitivity detected output values P0-P5 (actual measurements) of the individual photosensitive elements p0-p5 of the optical sensor 21 and the individual integral values S0-S5 obtained by integrating the distribution function P(x) within the range corresponding to the light-sensitive areas of the individual photosensitive elements p0-p5.

Since the integral value S is calculated by equation (3) in the above-described manner, the photosensitive elements pn entirely overlapping the integration range W are selected, and the integral value S can be corrected by multiplying the integral value S by a ratio R (=Up/Us) of a sum Up of the output values Pn of the selected photosensitive elements pn to a sum Us of integral values Sn obtained by integrating the distribution function P(x) within a range corresponding to the light-sensitive areas of the selected photosensitive elements pn. In the example of FIGS. 5A-5C, the integral value S is corrected by multiplying the integral value S by the ratio R which is equal to (P2+P3)/(S2+S3). Alternatively, the integral value S is corrected by multiplying the integral value S by the ratio R which is equal to (P2+P3+P4)/(S2+S3+S4).

Furthermore, although the optical property measuring apparatus 1 of the above-described embodiment is so configured as to determine the optical property by approximating the outputs of the optical sensor 21 by using the single distribution function P(x), the optical property measuring apparatus 1 may be so modified as to produce plural kinds of distribution functions P(x) indicating a distribution of the outputs of the optical sensor 21, or the amounts of the reflected light received by the optical sensor 21, and select one of the plural kinds of distribution functions P(x) best approximating the distribution of the amounts of the reflected light incident on the optical sensor 21 as the distribution function P(x) to be integrated within the aforementioned specific range (integration range W). The optical property measuring apparatus 1 thus configured makes it possible to measure the optical property with yet higher accuracy by determining the optical property by using the distribution function P(x) more accurately approximating the distribution of the amounts of the reflected light incident on the optical sensor 21. For example, the optical property calculator 31c of the control unit 31 approximates the outputs of the optical sensor 21 by the distribution function P(x) of equation (1) and that of equation (4) in this modified configuration. Then, the control unit 31 of this optical property measuring apparatus 1 compares values of D given equation (2) using the individual distribution functions P(x) and selects one of the plural kinds of distribution functions P(x) that gives the smallest value of D as the distribution function P(x) best approximating the outputs of the optical sensor 21.

Figure 6:
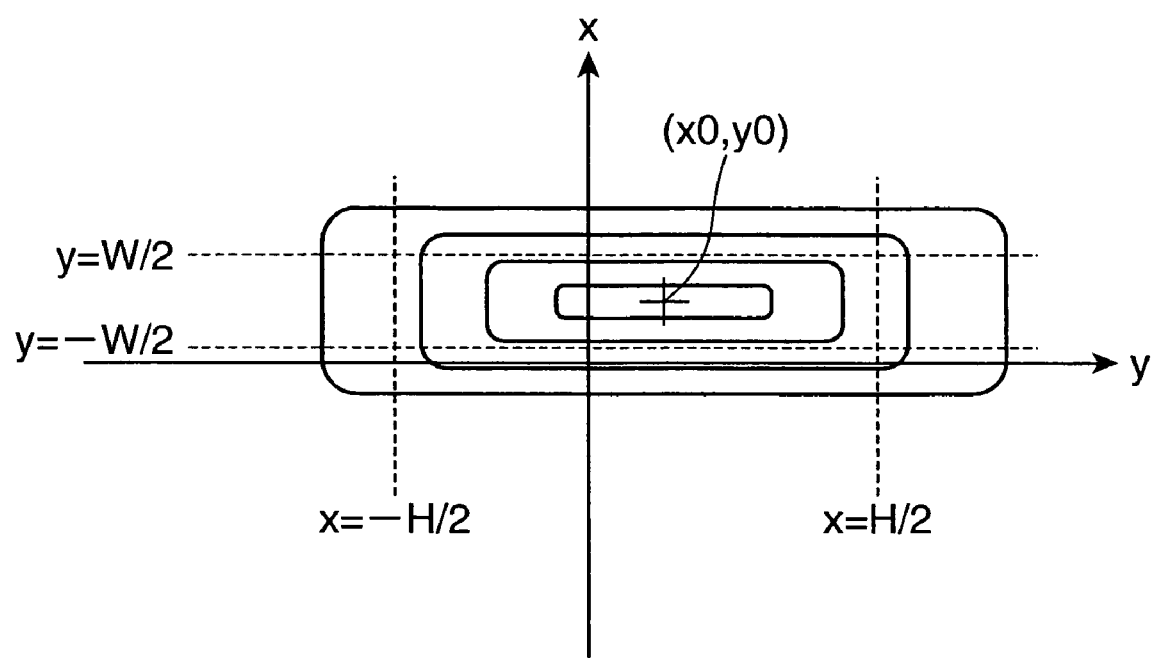
FIG. 6 is a diagram for explaining how an image of an aperture made in the aperture plate is formed on a light-sensing surface of the optical sensor.

FIG. 6 is a diagram showing an example of how the image of the aperture 12a made in the aperture plate 12 is formed on the light-sensing surface of the optical sensor 21. The image of the aperture 12a formed in the aperture plate 12 reflected by the sample surface SMa spreads out two-dimensionally on the light-sensing surface of the optical sensor 21 as illustrated in FIG. 6 if the surface SMa of the sample SM is not a specular surface. Here, it is assumed that the surface SMa of the sample SM is a specular surface and the image of the aperture 12a in the aperture plate 12 is formed on the light-sensing surface of the optical sensor 21. In the example of FIG. 6, a Cartesian xy-coordinate system is defined with x- and y-axes thereof corresponding to the directions of the width w and the height h of the aperture 12a, respectively, and with an origin of the Cartesian xy-coordinate system located at a central point of the sensing-side aperture 122a in the sensing-side aperture plate 122 of the prior art, assuming that this sensing-side aperture plate 122 is mounted in front of the optical sensor 21. Since the sample SM is displaced from the normal position in this example, the image of the aperture 12a in the aperture plate 12 spreads out two-dimensionally around a point with coordinates (x0, y0) as illustrated. Contour lines shown in FIG. 6 represent a distribution of intensities of the light incident on the light-sensing surface of the optical sensor 21.

The optical property measuring apparatus 1 of the above-described embodiment is so configured as to determine the optical property based on the distribution of the intensities of the light incident on the light-sensing surface of the optical sensor 21 along a direction corresponding to the direction of the width w (x-axis direction) of the aperture 12a provided that the surface SMa of the sample SM is a specular surface and the image of the aperture 12a in the aperture plate 12 is formed on the light-sensing surface of the optical sensor 21. Alternatively, the optical property measuring apparatus 1 may be so configured as to determine the optical property based on a distribution of the intensities of the light incident on the light-sensing surface of the optical sensor 21 along a direction corresponding to the direction of the height h (y-axis direction) of the aperture 12a provided that the surface SMa of the sample SM is a specular surface and the image of the aperture 12a in the aperture plate 12 is formed on the light-sensing surface of the optical sensor 21.

Still alternatively, the optical property measuring apparatus 1 may be so configured as to determine the optical property by producing a quadratic distribution function indicating a two-dimensional distribution of the intensities of the light incident on the light-sensing surface of the optical sensor 21 forming thereon the image of the aperture 12a in the aperture plate 12 as shown in FIG. 6. When the aperture 12a formed in the aperture plate 12 has a rectangular shape with the width w of 0.75 degrees and the height h of 2.5 degrees in terms of view angle, the optical sensor 21 is supposed to have an aperture measuring 4.4 degrees in width and 11.7 degrees in height in terms of view angle as discussed earlier with reference to the prior art configuration. Since the optical sensor 21 is supposed to provide a rectangular aperture which is elongate in the direction of height as mentioned above, the distribution of the intensities of the incident light in the x-axis direction is predominantly influential on the measurement of the optical property as can be seen from FIG. 6. It is however possible to measure the optical property with higher accuracy by using the two-dimensional distribution of the intensities of the light incident on the light-sensing surface of the optical sensor 21 taking into consideration the distribution of the intensities of the incident light in the y-axis direction.

Figure 7:
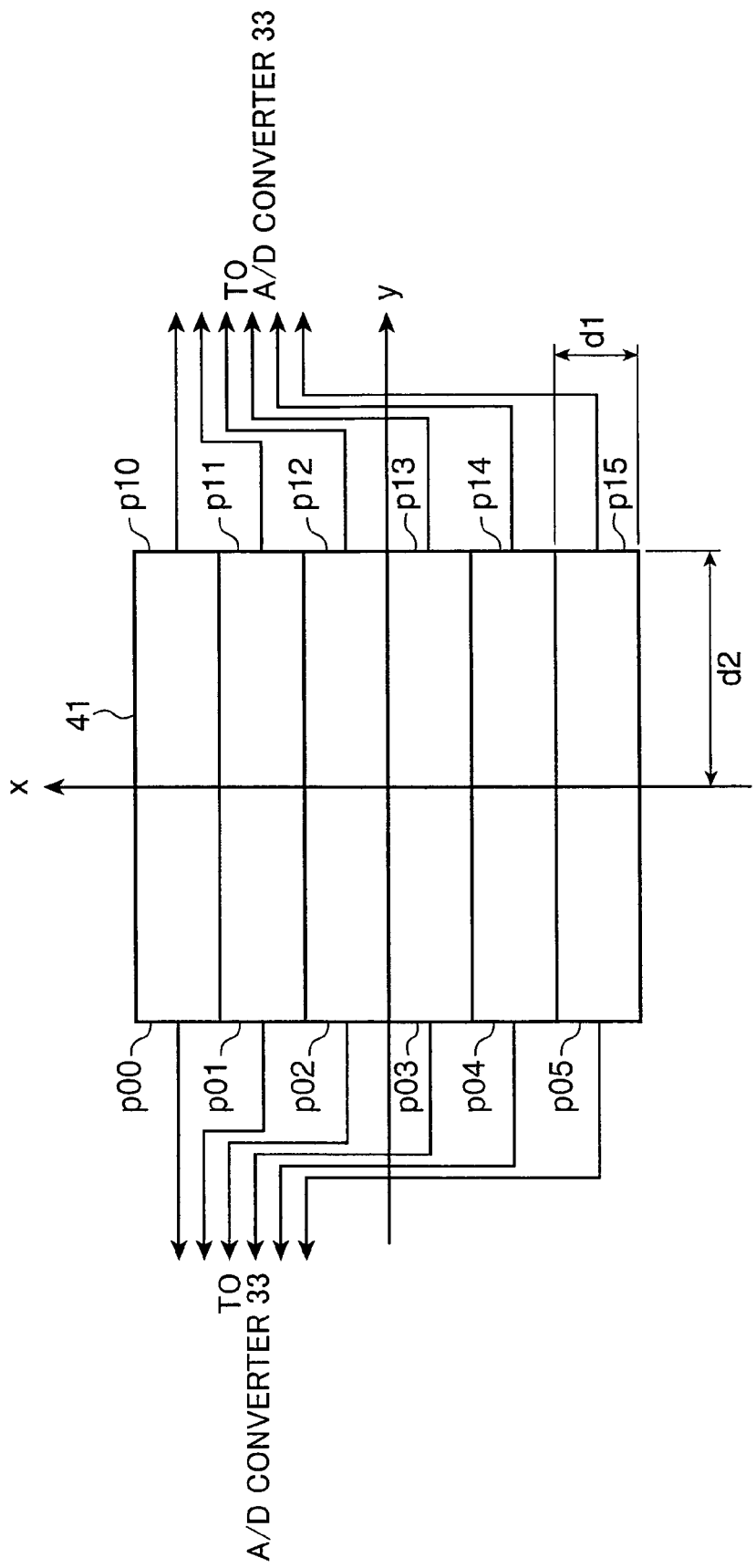
FIG. 7 is a diagram showing the configuration of an optical sensor employed in an optical property measuring apparatus in one variation of the preferred embodiment.

FIG. 7 is a diagram showing the configuration of an optical sensor used in an optical property measuring apparatus in one variation of the above-described preferred embodiment. This optical property measuring apparatus 1 employs the two-dimensional optical sensor 41 instead of the one-dimensional optical sensor 21 shown in FIG. 3. The two-dimensional optical sensor 41 includes a plurality of photosensitive elements which are photoelectric conversion elements for converting light energy into electrical energy. In this variation of the embodiment, the plurality of photosensitive elements are arranged along two linearly independent directions and the optical sensor 41 is configured such that outputs of the individual photosensitive elements can be directly taken out therefrom. The optical sensor 41 has a light-sensing surface which is larger than an area from which a specified optical property is to be determined, the optical sensor 41 including several to a little more than ten photosensitive elements. As the sample surface SMa illuminated by the projection-side optical system 10 reflects incident light and the optical sensor 41 receives part 21a of light reflected by the sample surface SMa generally in the direction of regular reflection, the individual photosensitive elements of the optical sensor 41 output electric signals corresponding to the amounts of received light.

Specifically, the optical sensor 41 of this variation of the embodiment is configured with a silicon photodiode array including two columns of six photosensitive elements p00-p05, p10-p15 of which analog outputs can be individually taken out, wherein the photosensitive elements p00-p05 (p10-p15) in each column are arranged along one of the aforementioned two linearly independent directions and the two columns are arranged side by side along the other direction perpendicular to the one direction, as illustrated in FIG. 7, for example. The optical sensor 41 is mounted at a location corresponding to the focal length f of the light-receiving lens 22 in such a manner that, when the surface SMa of the sample SM is a specular surface and an image of the aperture 12a in the aperture plate 12 is formed on the light-sensing surface of the optical sensor 41, the direction (x-axis direction) along which the photosensitive elements p00-p05 (p10-p15) in each column are arranged corresponds to the direction of the width w of the aperture 12a and the direction (y-axis direction) along which the two columns are arranged corresponds to the direction of the height h of the aperture 12a.

In the optical property measuring apparatus 1 of this variation of the embodiment, the optical property calculator 31c of the control unit 31 operates in the below-described fashion, for example. Specifically, the optical property calculator 31c produces a two-dimensional distribution function P(x, y) indicating a two-dimensional distribution of the amounts of the reflected light incident on the optical sensor 41 along linearly independent first and second coordinate axes (x- and y-axes shown in the example of FIG. 7) extending in the aforementioned photosensitive element arrangement directions on a plane defined on the light-sensing surface of the optical sensor 41 based on the outputs thereof, integrates the two-dimensional distribution function P(x, y) within a specific range and calculates the specified optical property of the sample SM based on an integral value S obtained by integrating the distribution function P(x, y).

The distribution of the amounts of light incident on the plane defined by the mutually perpendicular first and second coordinate axes on the light-sensing surface of the optical sensor 41 can be approximated by the two-dimensional distribution function P(x, y) which is expressed by equation (5) below, for example:

$$P(x, y) = \int_{x0-1/2}^{x0+1/2} \int_{y0-m/2}^{y0+m/2} F(x, y, a, b) da db \quad (5)$$

WHERE $F(x, y, a, b) = L \cdot \cos(\theta) + S \cdot \cos^N(\gamma)$ $\gamma = \sqrt{(\alpha - \alpha 0)^2 + (\beta - \beta 0)^2}$ $\theta = 60° - \alpha + \operatorname{atan}(x0/f)/2$ $\alpha = \operatorname{atan}(x/f)$ $\alpha 0 = \operatorname{atan}(a/f)$ $\beta = \operatorname{atan}(y/f)$ $\beta 0 = \operatorname{atan}(b/f)$ In equation (5) above, f designates the focal length of the light-receiving lens 22, (x0, y0) designates center coordinates of the distribution of the amounts of the reflected light incident on the optical sensor 41, N designates a numeral value which depends on the degree of glossiness of the sample surface SMa, L designates central intensity of the Lambertian diffuse light oriented about the direction of the normal G to the sample surface SMa, S designates central intensity of the scattered light oriented about the direction of regular reflection, l and m designate the widths of the image formed on the optical sensor 41 in the x- and y-axis directions when the sample surface SMa is a specular surface, and θ designates an angle that a ray of light incident at a coordinate x forms with the normal G to the sample surface SMa. The width m of a distribution in the y-axis direction can be approximated by the width l of a distribution in the x-axis direction and a ratio h/w of the height h to the width w of the aperture 12a by using m=l·(h/w). It is understood from above that the two-dimensional distribution function P(x, y) can be obtained by substituting the values of constants x0, y0, N, L, S and l in equation (5).

The two-dimensional distribution function P(x, y) can be produced based on the outputs of the individual photosensitive elements p00-p05, p10-p15 by essentially the same procedure as the earlier discussed procedure for producing the one-dimensional distribution function P(x). The aforementioned specific range (integration range) in which the two-dimensional distribution function P(x, y) is integrated is represented by a rectangular area centering on the point with the center coordinates (x0, y0) that corresponds to the rectangular sensing-side aperture 122a formed in the sensing-side aperture plate 122 of the earlier-described prior art having the width W of 4.4 degrees and the height H of 11.7 degrees in terms of view angle. Specifically, the aforementioned rectangular area corresponding to the integration range of the two-dimensional distribution function P(x, y) is a range of x0−W/2 to x0+W/2 in the x-axis direction and y0−H/2 to y0+H/2 in the y-axis direction bounded by broken lines in FIG. 6. A value of the optical property, such as glossiness, can be obtained from the integral value S calculated as described above by using a predefined conversion table or a conversion formula.

In the above-described variation of the embodiment, a distribution of intensities of light incident on the light-sensing surface of the optical sensor 41 forming thereon the image of the aperture 12a in the aperture plate 12 is expressed by the two-dimensional distribution function P(x, y). As an alternative, the optical property measuring apparatus 1 may be so configured as to produce first and second one-dimensional distribution functions indicating distributions of the amounts of the reflected light incident on the optical sensor 41 along the linearly independent first and second coordinate axes defined on the light-sensing surface of the optical sensor 41 and determine the optical property by using the first and second one-dimensional distribution functions. The optical property measuring apparatus 1 thus configured makes it possible to measure the specified optical property with higher accuracy. Additionally, the first and second one-dimensional distribution functions can be produced independently of each other with more ease by using a procedure simpler than the aforementioned procedure for producing the two-dimensional distribution function.

The optical property measuring apparatus 1 configured with this alternative arrangement employs, for example, the aforementioned optical sensor 41 shown in FIG. 7 instead of the optical sensor 21. In this optical property measuring apparatus 1, the optical property calculator 31c of the control unit 31 operates in the below-described fashion, for example. Specifically, the optical property calculator 31c produces the first and second one-dimensional distribution functions P(x), Q(y) indicating the distributions of the amounts of the reflected light incident on the optical sensor 41 along the linearly independent first and second coordinate axes (x- and y-axes shown in the example of FIG. 7) defined on the light-sensing surface of the optical sensor 41 based on the outputs thereof, integrates the first and second one-dimensional distribution functions P(x), Q(y) within specific ranges and calculates the specified optical property of the sample SM based on integral values Sp, Sq obtained by integrating the first and second one-dimensional distribution functions P(x), Q(y).

Figure 8:
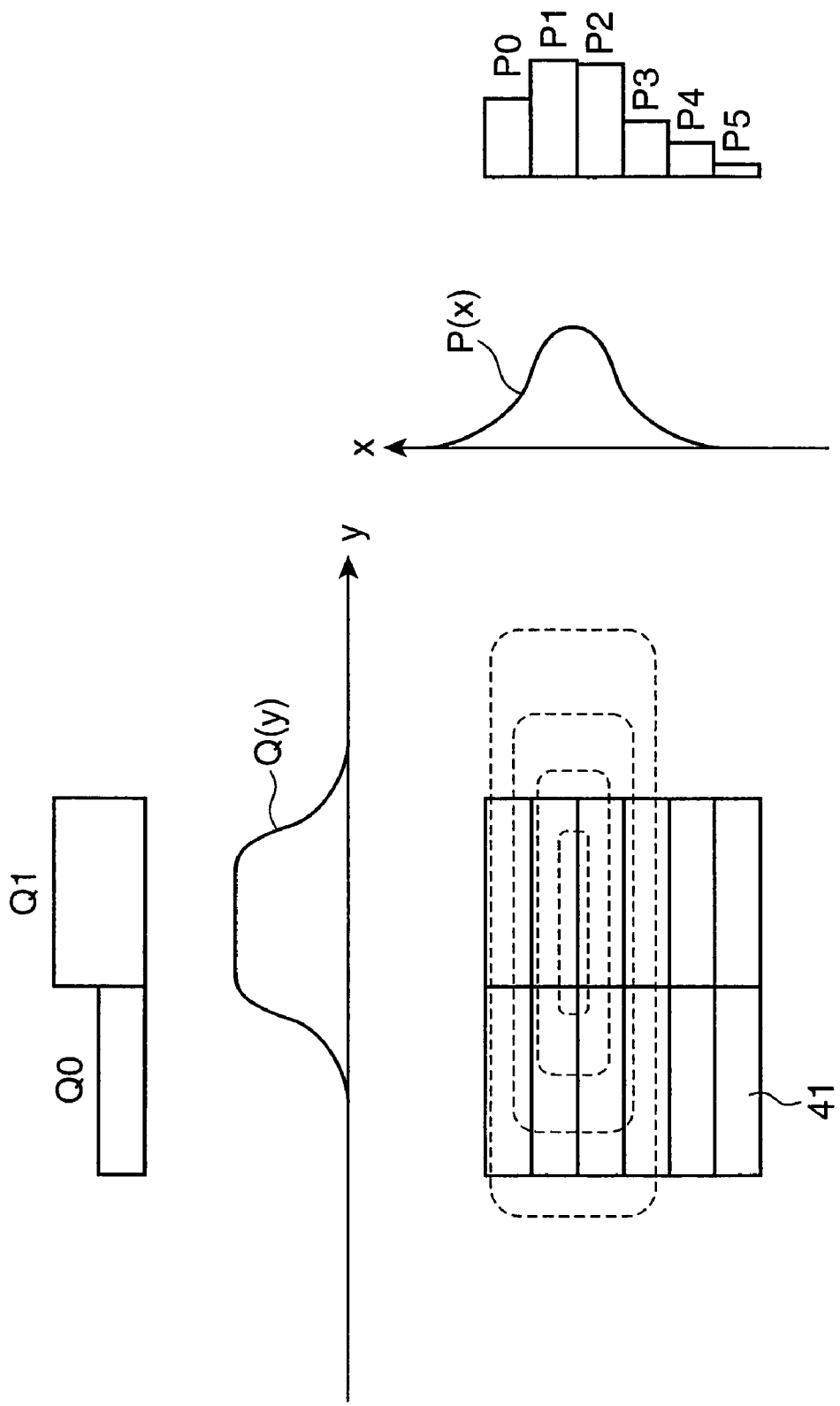
FIG. 8 is a diagram for explaining a procedure for producing distribution functions.
Figure 9:
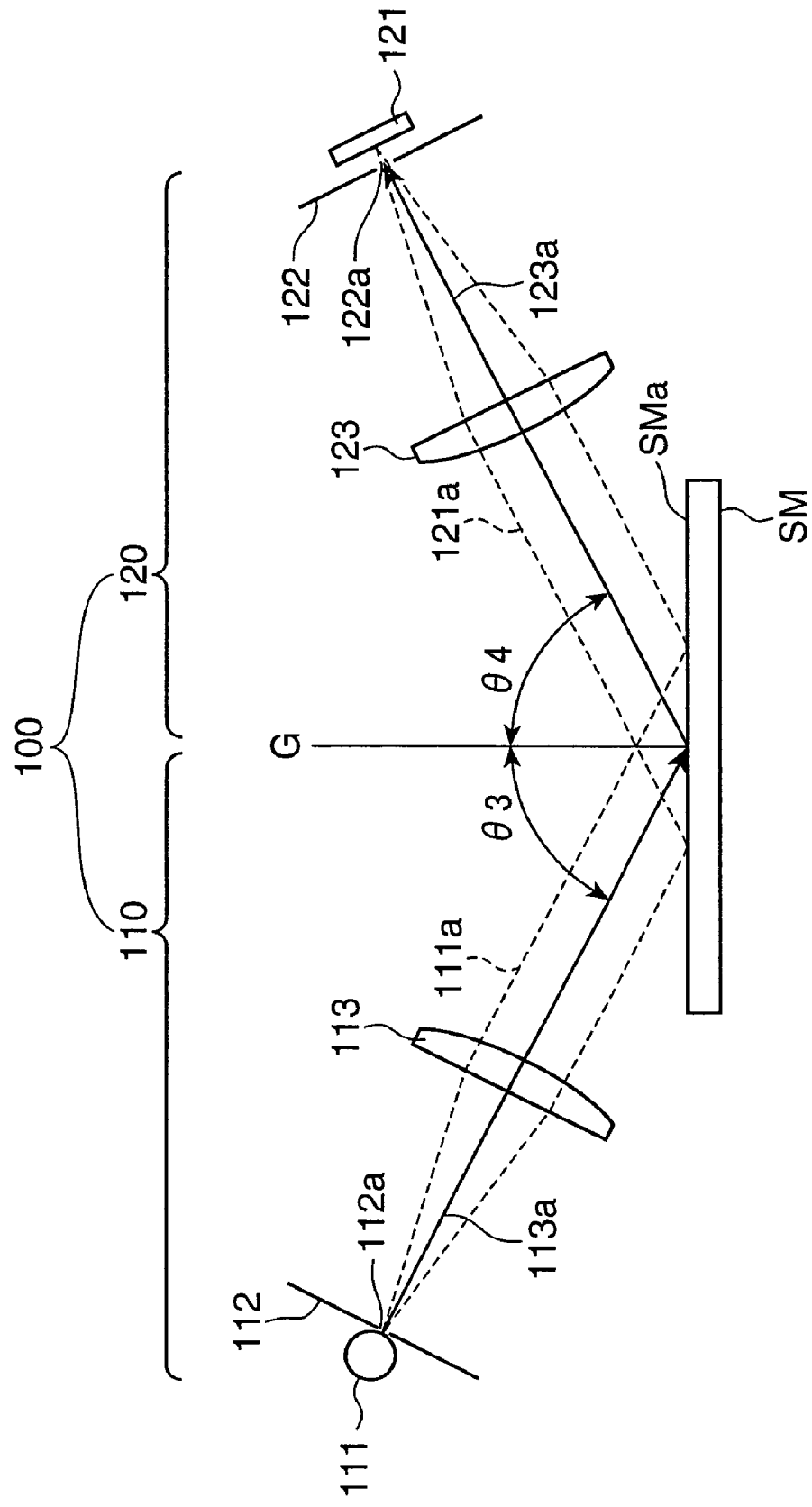
FIG. 9 is a diagram showing the optical configuration of a conventional optical property measuring apparatus.
Figure 10:
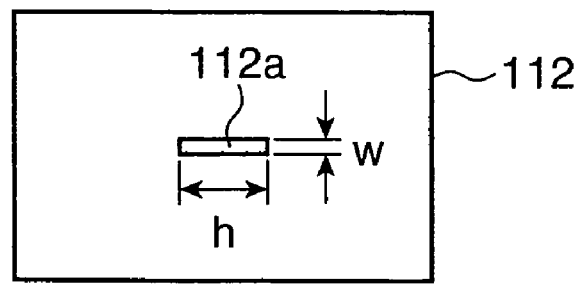
FIG. 10 is a plan view showing the structure of a projection-side aperture plate of the conventional optical property measuring apparatus.

The first and second one-dimensional distribution functions P(x), Q(y) can be produced based on the outputs of the individual photosensitive elements p00-p05, p10-p15 by essentially the same procedure as the earlier discussed procedure for producing the one-dimensional distribution function P(x). FIG. 8 is a diagram for explaining the procedure for producing the first and second one-dimensional distribution functions. For example, the first one-dimensional distribution function P(x) is produced based on row outputs P0-P5 of the photosensitive elements in individual rows, wherein each row output Pn (n=0, 1, 2, 3, 4, 5) is the sum of outputs of the photosensitive elements P0n and P1n in the same row. Also, the second one-dimensional distribution function Q(y) is produced based on a column output Q0 which is the sum of the outputs of the photosensitive elements p00-p05 and a column output Q1 which is the sum of the outputs of the photosensitive elements p10-p15.

The aforementioned specific range (integration range) in which the first one-dimensional distribution function P(x) is integrated is the range of x0−W/2 to x0+W/2 corresponding to the width W (=4.4 degrees) of the sensing-side aperture 122a formed in the sensing-side aperture plate 122 of the earlier-described prior art, wherein this range (x0−W/2 to x0+W/2) is centered on the x-coordinate x0 of the point with the center coordinates (x0, y0) of the rectangular area bounded by the broken lines in FIG. 6. On the other hand, the aforementioned specific range (integration range) in which the second one-dimensional distribution function Q(y) is integrated is the range of y0−H/2 to y0+H/2 corresponding to the height H (=11.7 degrees) of the sensing-side aperture 122a formed in the sensing-side aperture plate 122 of the earlier-described prior art, wherein this range (y0−H/2 to y0+H/2) is centered on the y-coordinate y0 of the point with the center coordinates (x0, y0) of the rectangular area bounded by the broken lines in FIG. 6. A value of the optical property, such as glossiness, can be obtained from a product Sp·Sq of the integral value Sp of the distribution function P(x) and the integral value Sq of the distribution function Q(y) calculated as described above by using a predefined conversion table or a conversion formula.

The aforementioned first and second one-dimensional distribution functions P(x), Q(y) can be obtained from equations (6-1) and (6-2) below, for example:

$$P(x) = \int_{x0-l/2}^{x0+l/2} F(x, a)\,da \quad (6\text{-}1)$$

WHERE $F(x, a) = L \cdot \cos(\theta) + S \cdot \cos^N(\alpha - \alpha0)$ $\alpha = \operatorname{atan}(x/f)$ $\alpha0 = \operatorname{atan}(a/f)$ $\theta = 60° - \alpha + \operatorname{atan}(x0/f)/2$ $$Q(y) = \int_{y0-m/2}^{y0+m/2} G(y, b)\,db \quad (6\text{-}2)$$

WHERE $G(y, b) = L \cdot \cos(\theta) + S \cdot \cos^N(\beta - \beta0)$ $\beta = \operatorname{atan}(y/f)$ $\beta0 = \operatorname{atan}(b/f)$ $\theta = 60° - \alpha + \operatorname{atan}(x0/f)/2$ The width m of a distribution of the second one-dimensional distribution function Q(y) can be approximated by the width l of a distribution of first one-dimensional distribution function P(x) and the ratio h/w of the height h to the width w of the aperture 12a by using m=l(h/w). Therefore, the optical property calculator 31c of the control unit 31 can determine the y-coordinate y0 of the point with the center coordinates (x0, y0) in the same way as for the distribution function P(x) based on the column outputs Q0, Q1.

If the first and second one-dimensional distribution functions P(x), Q(y) have a common formulaic pattern as shown in equations (6-1) and (6-2) above and constants N, L and S, among all constants defining the distribution functions P(x), Q(y), have the same value, it is possible to reduce the number of constants to be determined, and thus the number of the photosensitive elements, making it possible to simplify mathematical processing operation.

While the first and second one-dimensional distribution functions P(x), Q(y) have the common formulaic pattern as explained in the foregoing discussion, the distribution functions P(x), Q(y) may be formulated to have different patterns.

When the distribution of intensities of light incident on the light-sensing surface of the optical sensor 41 forming thereon the image of the aperture 12a in the aperture plate 12 is to be treated two-dimensionally as discussed above, the optical property measuring apparatus 1 may be so configured as to correct the integral values in the same way that the one-dimensional light intensity distribution is treated. Furthermore, the optical property measuring apparatus 1 may be so configured as to produce plural kinds of two-dimensional distribution function P(x, y) or first and second one-dimensional distribution functions P(x), Q(y) indicating the distribution of the amounts of the reflected light received by the optical sensor 41 and use the distribution function(s) best approximating the distribution of the amounts of the detected light.

While the present Specification has thus far described various arrangements of the art with reference to the preferred embodiment and variations thereof, principal arrangements of the art are summarized hereinbelow.

According to an aspect of the invention, an optical property measuring apparatus comprises a light source for projecting light on a sample to be measured, an optical sensor including a plurality of photosensitive elements for detecting the light projected by the light source and reflected by the sample, and a processor for determining a specified optical property of the sample based on an output of the optical sensor. In this optical property measuring apparatus, the processor produces a distribution function indicating a distribution of the amounts of the reflected light incident on the optical sensor along a coordinate axis defined on a light-sensing surface of the optical sensor based on the output thereof, integrates the distribution function within a specific range and determines the specified optical property based on an integral value obtained by integrating the distribution function.

According to another aspect of the invention, an optical property measuring method measures a specified optical property of a sample by using an optical property measuring apparatus comprising a light source for projecting light on the sample to be measured, an optical sensor including a plurality of photosensitive elements for detecting the light projected by the light source and reflected by the sample, and a processor for determining the specified optical property of the sample based on an output of the optical sensor. This optical property measuring method comprises the steps of producing a distribution function indicating a distribution of the amounts of the reflected light incident on the optical sensor along a coordinate axis defined on a light-sensing surface of the optical sensor based on the output thereof, integrating the distribution function within a specific range, and determining the specified optical property based on an integral value obtained by integrating the distribution function.

In the optical property measuring apparatus and the optical property measuring method of the invention configured as mentioned above, the distribution function indicating the distribution of the amounts of the reflected light incident on the optical sensor along the coordinate axis defined on the light-sensing surface of the optical sensor is produced based on the output thereof and integrated within the specific range, and the specified optical property is determined based on the integral value obtained by integrating the distribution function. As an example, the processor produces a distribution function approximating the output of the optical sensor, the distribution function containing positions of the photosensitive elements of the optical sensor and outputs of the respective photosensitive elements as independent variables and dependent variables, respectively, integrates the distribution function within the specific range and determines the specified optical property of the sample based on an integral value obtained by integrating the distribution function. Therefore, even when the optical sensor is a light-sensing device provided with a relatively small number of photosensitive elements, it is possible to measure the specified optical property regardless of a position error of the sample, if any, and reduce errors in measurement values caused by such a sample position error.

In one aspect of the invention, the optical property measuring apparatus further comprises a setter for setting an integration range. The integration range corresponds to an aperture standardized for the measurement of the specified optical property, with a center of the integration range being a centroid of the distribution function.

In another aspect of the invention, the optical property measuring apparatus is configured preferably in such a manner that the plurality of photosensitive elements of the optical sensor are arranged along two linearly independent directions, the processor produces a two-dimensional distribution function indicating the distribution of the amounts of the reflected light incident on the optical sensor along first and second coordinate axes extending in the aforementioned two linearly independent directions on a plane defined by the first and second coordinate axes on the light-sensing surface of the optical sensor based on the output thereof, integrates the two-dimensional distribution function within the specific range, and determines the specified optical property of the sample based on the integral value obtained by integrating the two-dimensional distribution function.

The reflected light incident on the optical sensor normally spreads two-dimensionally. According to the optical property measuring apparatus configured as mentioned above, the processor approximates the distribution of the amounts of the reflected light incident on the optical sensor by a two-dimensional distribution function, so that the specified optical property of the sample can be measured with higher accuracy.

In another aspect of the invention, the optical property measuring apparatus is configured preferably in such a manner that the plurality of photosensitive elements of the optical sensor are arranged along two linearly independent directions, the processor produces a combination of first and second one-dimensional distribution functions indicating the distribution of the amounts of the reflected light incident on the optical sensor along first and second coordinate axes extending in the aforementioned two linearly independent directions based on the output of the optical sensor, integrates each of the one-dimensional distribution functions within the specific range, and determines the specified optical property of the sample based on the integral value obtained by integrating each of the one-dimensional distribution functions.

According to the optical property measuring apparatus configured as mentioned above, the processor produces the first and second one-dimensional distribution functions indicating the distribution of the amounts of the reflected light incident on the optical sensor along the first and second coordinate axes extending in the two linearly independent directions. This makes it possible to measure the specified optical property of the sample with higher accuracy. Additionally, the first and second one-dimensional distribution functions can be produced independently of each other with more ease by using a procedure simpler than the aforementioned procedure for producing the two-dimensional distribution function.

In another aspect of the invention, the aforementioned first and second one-dimensional distribution functions preferably have a common pattern and contain a common constant when expressed in general formula.

According to this configuration, the first and second one-dimensional distribution functions have a common formulaic pattern and contain a common constant when expressed in general form, so that it possible to simplify mathematical processing operation for producing the first and second one-dimensional distribution functions.

In another aspect of the invention, the aforementioned one-dimensional distribution functions preferably contain a term indicating a distribution of the amounts of Lambertian diffuse light and a term indicating a distribution of the amounts of scattered light oriented about a direction of specular reflection.

According to this configuration, both the Lambertian diffuse light and the scattered light oriented about the direction of specular reflection are taken into consideration in the one-dimensional distribution functions indicating the distribution of the amounts of the reflected light incident on the optical sensor, so that it possible to approximate the distribution of the amounts of the reflected light incident on the optical sensor more properly.

In another aspect of the invention, the term of the aforementioned one-dimensional distribution functions indicating the distribution of the amounts of the scattered light oriented about the direction of specular reflection is expressed preferably by using earlier-mentioned equation (1) or (2) as basic form.

According to this configuration, it possible to approximate the distribution of the amounts of the scattered light oriented about the direction of specular reflection incident on the optical sensor, and thus the distribution of the total amounts of the reflected light on the optical sensor, more properly.

In another aspect of the invention, the processor preferably produces plural kinds of distribution functions and selects one of the plural kinds of distribution functions best approximating the distribution of the amounts of the reflected light incident on the optical sensor as the distribution function to be integrated within the specific range.

According to this configuration, the distribution of the amounts of the reflected light incident on the optical sensor is expressed by the plural kinds of distribution functions having different formulaic patterns and one of the plural kinds of distribution functions best approximating the distribution of the amounts of the reflected light incident on the optical sensor is selected as the distribution function used for determining the specified optical property. It is therefore possible to measure the specified optical property of the sample with higher accuracy.

In still another aspect of the invention, the processor preferably corrects the aforementioned integral value based on the output of the optical sensor.

According to this configuration, the integral value obtained by integrating the distribution function within the specific range is corrected, so that it is possible to measure the specified optical property of the sample with higher accuracy.

In yet another aspect of the invention, the optical sensor is configured preferably with a photodiode array.

In another aspect of the invention, the optical property measuring apparatus produces the distribution function indicating the distribution of the amounts of the reflected light incident on the optical sensor and determines the specified optical property of the sample by using the distribution function. This aspect of the invention makes it possible to use a photodiode array which offers superb basic performance with respect to S/N ratio of an output, linearity and temperature characteristics. Since the photodiode array having such superb basic performance is used as the optical sensor in the optical property measuring apparatus of the invention, it is possible to measure the specified optical property of the sample with higher accuracy as compared to a case where the optical sensor employs a charge-transfer image pickup device.

According to an aspect of invention, an optical property measuring apparatus comprises a light source for projecting light on a sample to be measured, an optical sensor including a plurality of photosensitive elements for detecting the light projected by said light source and reflected by the sample, and a processor for determining a specified optical property of the sample based on an output of said optical sensor the processor produces the optical property of the sample by integrating the distribution function obtained based on the output from said plurality of photosensitive elements along a coordinate axis defined on a light-sensing surface of said optical sensor within a specific range.

While the present invention has thus far been described properly and sufficiently through a discussion of the illustrative embodiment with reference to the drawings, it should be recognized that modifications and/or improvements of the embodiment can easily be done by those skilled in the art. It is therefore construed that such modifications and/or improvements fall within metes and bounds of the claims as long as the modifications and/or improvements do not constitute a departure from the spirit and scope of the claims.

What is claimed is:

1. An optical property measuring apparatus comprising:
   a light source for projecting light on a sample to be measured;
   an optical sensor including a plurality of photosensitive elements for detecting the light projected by the light source and reflected by the sample; and
   a processor for determining a specified optical property of the sample based on an output of the optical sensor;
   wherein the processor produces a mathematical distribution function indicating a spatial distribution of amounts of the reflected light incident on the optical sensor along a coordinate axis defined on a light-sensing surface of the optical sensor based on an output of the optical sensor, integrates the mathematical distribution function within a specific spatial range and determines the specified optical property based on an integral value obtained by integrating the mathematical distribution function.

2. The optical property measuring apparatus according to claim 1, further comprising;
   a setter for setting the specific range;
   wherein the specific spatial range corresponds to an aperture standardized for measurement of the specified optical property, with a center of the specific spatial range being a centroid of the mathematical distribution function.

3. The optical property measuring apparatus according to claim 1, wherein the plurality of photosensitive elements of the optical sensor are arranged along two linearly independent directions, wherein the mathematical distribution function produced by the processor is a two-dimensional spatial distribution function indicating the spatial distribution of the amounts of the reflected light incident on the optical sensor along first and second coordinate axes extending in the two linearly independent directions on a plane defined by the first and second coordinate axes and on the light-sensing surface of the optical sensor based on the output of the optical sensor, integrates the two-dimensional spatial distribution function within the specific range, and determines the specified optical property of the sample based on the integral value obtained by integrating the two-dimensional spatial distribution function.

4. The optical property measuring apparatus according to claim 1, wherein the plurality of photosensitive elements of the optical sensor are arranged along two linearly independent directions, wherein the mathematical distribution function produced by the processor is a combination of first and second one-dimensional spatial distribution functions indicating the spatial distribution of the amounts of the reflected light incident on the optical sensor along first and second coordinate axes extending in the two linearly independent directions based on the output of the optical sensor, integrates each of the first and second one-dimensional spatial distribution functions within the specific range, and determines the specified optical property of the sample based on the integral value obtained by integrating each of the first and second one-dimensional spatial distribution functions.

5. The optical property measuring apparatus according to claim 4, wherein the first and second one-dimensional spatial distribution functions have a common pattern and contain a common constant when expressed in general formula.

6. The optical property measuring apparatus according to claim 4, wherein the first and second one-dimensional spatial distribution functions contain a term indicating a spatial distribution of the amounts of Lambertian diffuse light and a term indicating a spatial distribution of the amounts of scattered light oriented about a direction of specular reflection.

7. The optical property measuring apparatus according to claim 6, wherein the term of the first and second one-dimensional spatial distribution functions indicating the spatial distribution of the amounts of the scattered light oriented about the direction of specular reflection is expressed by using an equation below as basic form:

$$Fs(x) = S \cdot \cos^N(\alpha - \alpha 0)$$

WHERE $$\alpha = a\tan(x/f)$$

$$\alpha 0 = a\tan(a/f)$$

x designates a coordinate on one of the first and second coordinate axes, a designates a center coordinate of a spatial distribution of intensities of the reflected light incident on the optical sensor, f designates a focal length of a light-receiving lens located between the sample and the-optical sensor for converging the reflected light from the sample onto the optical sensor, N designates a numeral value which depends on a degree of surface glossiness of the sample, and S designates central intensity.

8. The optical property measuring apparatus according to claim 6, wherein the term of the first and second one-dimensional spatial distribution functions indicating the spatial distribution of the amounts of the scattered light oriented about the direction of specular reflection is expressed by using an equation below as basic form:

$$Fs(x) = S \cdot \exp((-\tfrac{1}{2}) \cdot (\alpha - \alpha 0)^2 / d^2)$$

WHERE $$\alpha = a\tan(x/f)$$

$$\alpha 0 = a\tan(a/f)$$

x designates a coordinate on one of the first and second coordinate axes, a designates a center coordinate of a spatial distribution of intensities of the reflected light incident on the optical sensor, f designates a focal length of a light-receiving lens located between the sample and the optical sensor for converging the reflected light from the sample onto the optical sensor, d designates a numeral value which depends on a degree of surface glossiness of the sample, and S designates central intensity.

9. The optical property measuring apparatus according to claim 1, wherein the processor produces plural kinds of spatial distribution functions and selects one of the plural kinds of spatial distribution functions best approximating the spatial distribution of the amounts of the reflected light incident on the optical sensor as the spatial distribution function to be integrated within the specific range.

10. The optical property measuring apparatus according to claim 1, wherein the processor corrects the integral value based on the output of the optical sensor.

11. The optical property measuring apparatus according to claim 1, wherein the optical sensor is configured with a photodiode array.

12. The optical property measuring apparatus according to claim 1, wherein there is no aperture plate between the sample and the optical sensor.

13. An optical property measuring method for measuring a specified optical property of a sample by using an optical property measuring apparatus comprising a light source for projecting light on the sample to be measured, an optical sensor including a plurality of photosensitive elements for detecting the light projected by the-light source and reflected by the sample, and a processor for determining the specified optical property of the sample based on an output of the optical sensor, the optical property measuring method comprising the steps of:
producing a mathematical distribution function indicating a spatial distribution of the amounts of the reflected light incident on the optical sensor along a coordinate axis defined on a light-sensing surface of the optical sensor based on the output of the optical sensor;
integrating the mathematical distribution function within a specific spatial range; and
determining the specified optical property based on an integral value obtained by integrating the mathematical distribution function.

14. The method according to claim 13, wherein there is no aperture plate between the sample and the optical sensor.

15. An optical property measuring apparatus comprising:
a light source for projecting light on a sample to be measured;
an optical sensor including a plurality of photosensitive elements for detecting the light projected by the light source and reflected by the sample; and
a processor for determining a specified optical property of the sample based on an output of the optical sensor;
wherein the processor determines the specified optical property of the sample by integrating a mathematical distribution function obtained based on the output from the optical sensor along a coordinate axis defined on a light-sensing surface of the optical sensor within a specific spatial range.

16. The optical property measuring apparatus according to claim 15, wherein there is no aperture plate between the sample and the optical sensor.

* * * * *